United States Patent [19]

Tozawa et al.

[11] Patent Number: 4,665,059

[45] Date of Patent: May 12, 1987

[54] COMPOSITION FOR REDUCING THE PHYTOTOXICITY OF AGRICULTURAL MACHINE OIL CONTAINING A SUCROSE FATTY ACID ESTER AND/OR UREA

[75] Inventors: Takashi Tozawa, Yokohama; Masahiro Endo, Zama; Yukio Eiraku, Ogori, all of Japan

[73] Assignee: Mitsubishi Chemical Industries, Ltd., Tokyo, Japan

[21] Appl. No.: 707,412

[22] Filed: Mar. 1, 1985

Related U.S. Application Data

[63] Continuation of Ser. No. 564,188, Dec. 22, 1983, Pat. No. 4,541,859.

[30] Foreign Application Priority Data

Dec. 28, 1982 [JP]  Japan .................................. 57-234536

[51] Int. Cl.$^4$ ................................................ A61K 31/70
[52] U.S. Cl. ............................................. 514/53; 71/88; 71/127; 71/DIG. 1; 514/762
[58] Field of Search ............... 514/53; 536/119; 71/88

[56] References Cited

U.S. PATENT DOCUMENTS

| | | | |
|---|---|---|---|
| 3,996,206 | 12/1976 | Parker et al. | 536/119 |
| 4,165,230 | 8/1979 | Gravrok et al. | 514/772 |
| 4,336,052 | 6/1982 | Chen et al. | 71/DIG. 1 |

Primary Examiner—Johnnie R. Brown
Assistant Examiner—Elli Peselev
Attorney, Agent, or Firm—Oblon, Fisher, Spivak, McClelland & Maier

[57] ABSTRACT

A method for reducing the phytotoxicity of agricultural machine oil in its application to an agricultural or horticultural plant to exterminate noxious insects and acarines, characterized in that, prior to or at the same time as the application of the machine oil, a sucrose fatty acid ester is applied to the agricultural or horticultural plant in an amount of from 0.1 to 50 parts by weight per 100 parts by weight of the machine oil, in the form of an aqueous solution containing from 0.001 to 1 wt/v % of the ester.

7 Claims, No Drawings

COMPOSITION FOR REDUCING THE PHYTOTOXICITY OF AGRICULTURAL MACHINE OIL CONTAINING A SUCROSE FATTY ACID ESTER AND/OR UREA

This is a continuation of application Ser. No. 564,188, filed Dec. 22, 1983, now U.S. Pat. No. 4,541,859.

The present invention relates to a method for reducing the phytotoxicity by agrochemicals, which frequently occurs when an agricultural machine oil is applied to plants alone or in combination with other agricultural chemicals by combined application or short interval application, and to an insecticidal and acaricidal composition useful for the method.

The agricultural machine oil is mainly used for the extermination of scale insects or acarines breeding on fruit trees such as citrus, apple, peach or pear trees. Such machine oil is regarded as an important agricultural chemical, since it does not create any substantial resistance, which insects or acarines may acquire when conventional synthetic insecticides or acaricides are employed, and it is inexpensive. On the other hand, it is known that when applied to plants, the agricultural machine oil presents certain adverse effects or phytotoxicity to the plants. This is a main factor which limits the usefulness of the machine oil. As such adverse effects caused by the application of the agricultural machine oil, there may be mentioned oil specks formed on the surface of fruits and leaves, falling off of the leaves or the quality degradation of the fruits such as a decrease of a sugar content in the fruits, an increase of the acidity or inferior coloration. At the same time, the photosynthetic ability of the plant leaves will be substantially lowered by the application of the agricultural machine oil, and it is reported that it takes a few months for the recovery of the photosynthetic ability. Further, when used in combination with other agricultural chemicals for combined application or short interval application, the agricultural machine oil frequently serves to promote the phytotoxicity of the agricultural chemicals or gives rise to a phytotoxicity which does not appear when the agricultural chemicals are used alone independently. Thus, the usefulness of the machine oil is thereby substantially restricted.

In order to solve the above-mentioned problems, it has been proposed to improve the quality of the agricultural machine oil by refining it to lower the viscosity. By such a quality improvement, the adverse effects can be reduced to some extent. However, the production cost increases as the process requires an additional refining step. Further, the reduction of the adverse effets is not necessarily adequate.

On the other hand, it has been proposed to use surfactants for the reduction of the phytotoxicity (Japanese Examined Patent Publications No. 14613/1978 and No. 40688/1981). However, these proposals are intended to reduce the phytotoxicity of copper sulfate or copper chloride to plants by dispersing the copper sulfate or copper chloride in màchine oil in the presence of a nonionic surfactant.

The present invention has been accomplished as a result of extensive researches on various surfactants with an aim to reduce the phytotoxicity of the agricultural machine oil without impairing the insecticidal and acaricidal activities.

Namely, the present invention provides a method for reducing the phytotoxicity of agricultural machine oil, which is characterized in that a sucrose fatty acid ester is applied prior to or at the same time as the application of the agricultural machine oil. The present invention also provides a composition useful for the method. In a preferred embodiment of the present invention, urea is used in combination with the sucrose fatty acid ester.

Now, the present invention will be described in detail with reference to the preferred embodiments.

Various sucrose fatty acid esters are commercially available, in which the kind of the fatty acid or the degree of esterification varies. Any one of them may optionally be employed depending upon the particular purpose.

From the viewpoint of convenience for the preparation of a formulation by mixing it with the agricultural machine oil, the sucrose fatty acid ester should preferably have a low HLB. Whereas, from the viewpoint of the solubility and dispersibility in water for its application in a diluted form, it should preferably have a high HLB. The HLB may be at any level, when the sucrose fatty acid is used in combination with an emulsifier or a solvent for the preparation of a formulation or a diluted solution for application. However, the sucrose fatty acid ester preferably has a HLB of from 9 to 17. The fatty acid moiety thereof preferably has from 14 to 18 carbon atoms, and the monoester content in the sucrose fatty acid ester is preferably from 40 to 80%.

The agricultural machine oil is commercially available usually in the form of an emulsifiable concentration. At the time of the application, it is diluted with water and used in the form of an emulsion containing from 0.25 to 8 v/v % of the machine oil.

The sucrose fatty acid ester is usually applied in an amount of from 0.1 to 50 parts by weight, preferably from 0 5 to 20 parts by weight, per 100 parts by weight of the agricultural machine oil. The sucrose fatty acid ester of this amount is applied prior to or simultaneously with the application of the agricultural machine oil, in the form of an aqueous solution containing from 0.001 to 1 wt/v %, preferably from 0.01 to 0.2 wt/v %. In some cases, it may be used in the form of a mixture with the agricultural machine oil.

If the amount of the sucrose fatty acid ester is less than the above-mentioned range, the effectiveness for the reduction of the phytotoxicity tends to be small. On the other hand, if the amount exceeds the above- mentioned range, it will be necessary to increase the amount of the emulsifier or the solvent required for the preparation of the formulation.

When urea is to be employed in combination with the sucrose fatty acid ester, urea is usually used in an amount of from 1 to 300 parts by weight, preferably from 5 to 100 parts by weight, per 100 parts by weight of the agricultural machine oil, in the form of an aqueous solution containing from 0.01 to 5 wt/v % of the urea. If the amount of the urea is too small, no adequate effectiveness for the reduction of the phytotoxicity will be obtained. On the other hand, if the amount is excessive, the urea concentration at the time of the application will be unduly high, whereby it is likely to lead to an adverse effect to the plants.

In the present invention, the sucrose fatty acid ester may be used in combination with a conventional emulsifier, wettable powder, solvent, herbicide, fungicide, insecticide or fertilizer. Such an additive may be incorporated at the time of the application or during the preparation of the composition.

According to the present invention, an aqueous sucrose fatty acid ester is applied prior to the application of agricultural machine oil, or a composition comprising agricultural machine oil and a sucrose fatty acid ester is diluted with water and applied in the same manner as in the case of the application of usual agricultural machine oil, whereby it is possible to substantially reduce the phytotoxicity of the agricultural machine oil, such as formation of oil specks on the leaves and fruits, falling off of the leaves, degradation of the quality of the fruits such as a decrease of the sugar content, an increase of the acidity or inferior coloring of the fruits, or a decrease of photosynthetic ability of the leaves, which used to be caused by the application of agricultural machine oil. Further, it is thereby possible to reduce a phytotoxicity which is caused by combined application or short interval application of agricultural machine oil together with other agricultural chemicals such as 2,3-dithiano-1,4-dithianoneanthraquinone. The mechanism for the reduction of the phytotoxicity according to the process of the present invention is not clearly understood. It is likely, however, that the sucrose fatty acid ester serves to prevent the local concentration of agricultural chemicals such as agricultural machine oil resulting from the penetration and transfer of the agricultural chemicals in the leaves or the fruit surfaces, and to promote the proper function of various metabolisms in the plant body, and urea provides a nutrient as a nitrogen source and thus serves for the encouragement of the plants, whereby not only the emergence of the phytotoxicity is prevented but also the resistibility of the plants against the phytotoxicity is improved.

Now, the present invention will be described in further detail with reference to Examples. However, it should be understood that the present invention is by no means restricted by these specific Examples.

In the following Examples, Spindlon emulsifiable concentration manufactured by Mikasa Chemical Industry Co., Ltd. was used as the machine oil emulsifiable concentration, and Ryoto Sugar Esters (manufactured by Ryoto Co., Ltd.) as identified in the following Table 1 were used as the sucrose fatty acid esters.

TABLE 1

| Cane sugar esters | Trade-names Ryoto Sugar Esters | HLB | Bound fatty acids (%) Stearic acid | Palmitic acid | Oleic acid | Ester composition (%) Mono- ester | Di-, tri- ester |
|---|---|---|---|---|---|---|---|
| SE-1 | S-1570 | 15 | 70 | 30 | — | 70 | 30 |
| SE-2 | P-1570 | 15 | 30 | 70 | — | 70 | 30 |
| SE-3 | O-1570 | 15 | — | — | 70 | 70 | 30 |
| SE-4 | O- 570 | 5 | — | — | 70 | 35 | 65 |
| SE-5 | S- 570 | 5 | 70 | 30 |  | 35 | 65 |
| SE-6 | L-1540 | 15 | Laulic acid 50 | | | 70 | 30 |

EXAMPLES 1 to 6 and COMPARATIVE EXAMPLE

The machine oil emulsifiable concentration and SE-3 were diluted with water to bring the machine oil concentration to 1% (v/v) and the SE-3 concentration to those identified in Table 2, and they were dissolved to obtain emulsions for application. Each emulsion was applied to a potted three year old plant of Satsuma mandarine orange (Citrus unshiu Marc) so that the leaves were sufficiently wetted. Three days later, the formation of oil specks as a characteristic phytotoxicity of the machine oil emulsion was evaluated with respect to new leaves developed this year, in accordance with the evaluation standards as identified in Table 3.

The results thereby obtained are shown in Table 2. It is evident from Table 2 that in the case where the machine oil emulsifiable concentration was used alone, oil specks were formed on the leaf surface, whereas by the presence of the sucrose fatty acid ester, the formation of the oil specks was remarkable suppressed.

TABLE 2

|  | Concentration of SE-3 (%, w/v) | Degree of phytotoxicity |
|---|---|---|
| Comparative Example 1 | 0 | +++ |
| Example 1 | 0.0025 | ++ |
| Example 2 | 0.005 | + |
| Example 3 | 0.01 | + |
| Example 4 | 0.04 | + |
| Example 5 | 0.08 | + |
| Example 6 | 0.2 | ± |

TABLE 3

| Degree of phytotoxicity | Evaluation standards |
|---|---|
| +++ | Oil specks formed on at least 30% of the entire surface area of the leaf |
| ++ | Oil specks formed on 10–30% of the entire surface area of the leaf |
| + | Oil specks formed on less than 10% of the entire surface area of the leaf |
| ± | Oil specks slightly observed |

EXAMPLES 7 to 9

The machine oil emulsifiable concentration and various sucrose fatty acid esters as identified in Table 4 were diluted with water to bring their concentrations to 1% (v/v) and 0.01% (w/v), respectively, and they were dissolved to obtain emulsions for application. In the same manner as in Example 1, the application treatment was conducted, and the formation of the phytotoxicity was evaluated.

The results thereby obtained are shown in Table 4. If is evident from Table 4 that each kind of the sucrose fatty acid esters was effective in the reduction of the phytotoxicity.

TABLE 4

|  | Cane sugar esters | Degree of phytotoxicity |
|---|---|---|
| Comparative Example 1 | — | +++ |
| Example 7 | SE-1 | + |
| Example 8 | SE-2 | + |
| Example 9 | SE-4 | + |

EXAMPLES 10 and 11

The machine oil emulsifiable concentration and SE-3 were diluted with water to bring their concentrations to 1% (v/v) and 0.08% (w/v), respectively, and they were dissolved to obtain an emulsion for application. Another emulsion was prepared in the same manner except that 1% (w/v) of urea was added. In the same manner as in Example 1, these emulsions were applied, and the formation of the phytotoxicity was evaluated.

The results thereby obtained are shown in Table 5. It is evident from Table 5 that the phytotoxicity can further be reduced by the combination of the sucrose fatty acid ester with urea.

TABLE 5

|  | Concentration of SE-3 (%, w/v) | Concentration of urea (%, w/v) | Degree of phytotoxicity |
|---|---|---|---|
| Comparative Example 1 | 0 | 0 | +++ |
| Example 10 | 0.08 | 0 | + |
| Example 11 | 0.08 | 1 | ± |

EXAMPLES 12 to 14 and COMPARATIVE EXAMPLE 2

The machine oil emulsifiable concentration, SE-3 and urea were diluted with water to bring their concentrations to the respective values as identified in Table 6, and they were dissolved to obtain emulsions for application. Each emulsion was applied to a potted three years old plant of Satsuma mandarine orange so that the leaves were adequately wetted. The photosynthesis rates were measured prior to the application, one day after the application and four days after the application. The results thereby obtained are shown in Table 6, in which the photosynthesis rates are represented by the relative values based on the photosynthesis rate prior to the application being taken as 100.

The measurement of the photosynthesis rates was conducted by placing the sample plants in a closed phytotron (30°C.) and measuring the change of the carbondioxide concentration in the phytotron by means of an infrared gas analyzer. The apparent photosynthesis rate was obtained from the reducing rate of the carbondioxide concentration under illumination, and the respiration rate was obtained from the increasing rate of the carbondioxide concentration under a blacked out condition. The sum of the apparent photosynthesis rate and the respiration rate was taken as the true photosynthesis rate. From the results of the measurement, it was found that by the application of the machine oil emulsion, the photosynthesis rate was remarkably reduced, whereas when the sucrose fatty acid ester was used in combination, the reduction of the photosynthesis rate is substantially moderated, and when urea was also used in combination, the reduction of the photosynthesis rate is further minimized.

TABLE 6

| | Compositions of the emulsions | | | Photosynthesis rates (Relative values) | | |
|---|---|---|---|---|---|---|
| | Machine oil emulsifiable concentration (%, v/v) | SE-3 (%, v/v) | Urea (%, v/v) | Prior to the application | One day after the application | 4 days after the application |
| Comparative Example 2 | 1 | 0 | 0 | 100 | 78 | 83 |
| Example 12 | 1 | 0.01 | 0 | 100 | 86 | 87 |
| Example 13 | 1 | 0.2 | 0 | 100 | 89 | 93 |
| Example 14 | 1 | 0.2 | 1 | 100 | 94 | 97 |

EXAMPLES 15 to 22 and COMPARATIVE EXAMPLES 3 to 15

By using the machine oil emulsifiable concentration, SE-3, urea, an insecticide (dimethoate emulsifiable concentration manufactured by Tomono Nohyaku Co., Ltd.) and a fungicide (Spatcide wettable powder manufactured by Kumiai Chemical Industry Co., Ltd.), comparative tests (Test Nos. 1-5) as shown in Table 7 were set up each for comparison of a combined application with a control. Test No. 6 is a blank test where no agricultural chemical was applied.

For each comparative test, three Satsuma mandarine orange trees of six years old were used. In each tree, a half thereof was used for testing the combined application and the other half was used for testing the control.

The concentrations of the chemicals in the emulsions for application were as follows: 1% (v/v) of the machine oil emulsifiable concentration, 0.08% (w/v) of SE-3, 1% (w/v) of urea, 0.1% (v/v) of the insecticide and 0.13% (w/v) of the fungicide.

In each comparative test, the application was conducted twice, i.e. the second application was made on the 37th day after the first application. Each time, the emulsions were applied by means of a sprayer so that the test tree leaves were adequately wetted (i.e. 2-2.3 liters per tree). After the second application, the phytotoxicities to new leaves, old leaves and fruits were evaluated by examination of the rate of oil-specked leaves or fruits in all leaves or fruits, and the number of fallen leaves was also investigated. The results thereby obtained are shown in Table 7.

Further, on the 77th day after the second application, ten fruits were taken from each half of each tree, and their weights, the sugar content and the citric acid content of the fruit juice were measured, and the coloring, the uniformity of the coloring and the stains of the fruit skin were examined. The results thereby obtained are shown in Table 8. The sugar content was measured by Brix sugar meter, and the citric acid content was obtained by calculating the amount of citric acid from the titer obtained by titration with a sodium hydroxide standard solution.

As shown in Table 7, the phytotoxicities to the leaves and fruits or the increase of the number of fallen leaves caused by the machine oil emulsifiable concentration or the combined use of the machine oil emulsifiable concentration with other agricultural chemicals, can be reduced to some extent by a combined use of urea. However, when the sucrose fatty acid ester or a combination of the sucrose fatty acid ester with urea was employed, the effectiveness for the reduction of the phytotoxicities becomes more distinct. On the other hand, with respect to the quality of the fruits, the combined use of urea gives certain effectiveness to prevent the decrease of the sugar content and the increase of citric acid, whereas when the sucrose fatty acid ester or a combination of the sucrose fatty acid ester with urea was employed, not only such effectiveness but also other effectiveness such as an increase of the weight of the fruits, good coloring and little stains, are obtainable.

TABLE 7

| | Test Nos. | Agricultural chemicals | Phytotoxicities | | | | | | Number of fallen leaves (Number/tree) |
|---|---|---|---|---|---|---|---|---|---|
| | | | Rate of oil-specked new leaves (%) | | Rate of oil-specked old leaves (%) | | Rate of oil-specked fruits (%) | | |
| | | | Number of days after the second application | | | | | | |
| | | | 7 days | 33 days | 7 days | 33 days | 7 days | 33 days | 7 days |
| Comparative Example 3 | 1 | Machine oil emulsifiable concentration | 88 | 75 | 93 | 50 | 98 | 42 | 4 |
| Example 15 | | Machine oil emulsifiable concentration + SE-3 | 72 | 53 | 43 | 25 | 60 | 7 | 1 |
| Comparative Example 4 | 2 | Machine oil emulsifiable concentration | 88 | 92 | 100 | 80 | 95 | 65 | 5 |
| Comparative Example 5 | | Machine oil emulsifiable concentration + Urea | 85 | 55 | 50 | 35 | 47 | 25 | 1 |
| Comparative Example 6 | 3 | Machine oil emulsifiable concentration | 100 | 72 | 92 | 43 | 47 | 40 | 4 |
| Example 16 | | Machine oil emulsifiable concentration + SE-3 + Urea | 75 | 25 | 48 | 18 | 15 | 3 | 1 |
| Comparative Example 7 | 4 | Machine oil emulsifiable concentration + Insecticide | 100 | 82 | 92 | 78 | 85 | 62 | 3 |
| Example 17 | | Machine oil emulsifiable concentration + Insecticide + SE-3 | 53 | 35 | 57 | 23 | 40 | 36 | 1 |
| Comparative Example 8 | 5 | Machine oil emulsifiable concentration + Bactericide | 67 | 37 | 80 | 27 | 48 | 48 | 4 |
| Example 18 | | Machine oil emulsifiable concentration + Bactericide + SE-3 | 32 | 35 | 35 | 18 | 34 | 13 | 1 |
| Comparative Example 9 | 6 | None | 0 | 0 | 0 | 0 | 0 | 0 | 0 |

TABLE 8

| | Test Nos. | Agricultural chemicals | Weight of the fruit (g) | Sugar (%) | Citric acid (%) | Sugar-acid ratio (Sugar/citric acid) | Coloring and fruit skin condition (as compared with the respective control) |
|---|---|---|---|---|---|---|---|
| Comparative Example 10 | 1 | Machine oil emulsifiable concentration | 113 | 7.0 | 1.3 | 5.4 | (Control) |
| Example 19 | | Machine oil emulsifiable concentration + SE-3 | 133 | 7.1 | 1.1 | 6.5 | Coloring-good Stains on the skin-little |
| Comparative Example 11 | 2 | Machine oil emulsifiable concentration | 142 | 7.0 | 1.3 | 5.4 | (Control) |
| Comparative Example 12 | | Machine oil emulsifiable concentration + Urea | 137 | 7.2 | 1.2 | 6.0 | Stains on the skin substantial |
| Comparative Example 13 | 3 | Machine oil emulsifiable concentration | 121 | 6.9 | 1.4 | 4.9 | (Control) |
| Example 20 | | Machine oil emulsifiable concentration + SE-3 + Urea | 124 | 7.0 | 1.3 | 5.4 | Coloring good and uniform Stains on the skin-little |
| Comparative Example 14 | 4 | Machine oil emulsifiable concentration + Insecticide | 106 | 6.9 | 1.5 | 4.6 | (Control) |
| Example 21 | | Machine oil emulsifiable concentration + Insecticide + SE-3 | 117 | 7.0 | 1.4 | 5.0 | Stains on the skin-little |
| Comparative Example 15 | 5 | Machine oil emulsifiable concentration + Bactericide | 110 | 6.7 | 1.5 | 4.5 | (Control) |
| Example 22 | | Machine oil emulsifiable concentration + Bactericide + SE-3 | 123 | 6.8 | 1.4 | 4.9 | Coloring-good |

EXAMPLES 23 to 26 and COMPARATIVE EXAMPLES 16 to 19

The effectiveness for the reduction of the phytotoxicities to Satsuma mandarine orange trees of six years old was compared with respect to the combined application or the short interval application of the machine oil emulsifiable concentration and a fungicide (Delan wettable powder containing 2,3-dithiano-1,4-dithianoneanthraquinone as the active ingredient, manufactured by Mikasa Chemical Industry Co., Ltd.).

For the combined application, emulsions for combined application as shown in Table 9 were prepared by using the machine oil emulsifiable concentration, the fungicide, urea and SE-3. Three orange trees were used for each of the four tests. The rate of formation of brown specks which started to form about one week after the application of each emulsion, was measured and presented in Table 9 as the phytotoxicity rate.

In the short interval application tests, the fungicide was firstly applied to all orange trees, as shown in Table 10. Twelve days after the first application, each of the four emulsions for the second application as identified in Table 10 was applied to three orange trees, respectively. Then, the phytotoxicity rate was determined in the same manner as mentioned above. The results thereby obtained are shown in Table 10.

From the results, it is evident that with respect to the effectiveness for the reduction of phytotoxicity in the combined and short interval applications, the combined use of urea is effective to some extent, whereas the combined use of the sucrose fatty acid ester presents remarkable effectiveness, and the combination of the sucrose fatty acid ester with urea further improves the effectiveness.

TABLE 9

| | Combined application | | | |
|---|---|---|---|---|
| | Machine oil emulsifiable concentration (%, v/v) | Bactericide (%, w/v) | SE-3 (%, w/v) | Urea (%, w/v) | Phytotoxicity rate (%) |
| Comparative Example 16 | 1.0 | 0.2 | — | — | 100 |
| Example 23 | 1.0 | 0.2 | 0.08 | — | 40 |
| Comparative Example 17 | 1.0 | 0.2 | — | 1.0 | 60 |
| Example 24 | 1.0 | 0.2 | 0.08 | 1.0 | 10 |

TABLE 10

| | First application | Second application | | | |
|---|---|---|---|---|---|
| | Bactericide (%, w/v) | Machine oil emulsifiable concentration (%, v/v) | SE-3 (%, w/v) | Urea (%, w/v) | Phytotoxicity rate (%) |
| Comparative Example 18 | 0.2 | 1.0 | — | — | 100 |
| Example 25 | 0.2 | 1.0 | 0.08 | — | 8 |
| Comparative Example 19 | 0.2 | 1.0 | — | 1.0 | 70 |
| Example 26 | 0.2 | 1.0 | 0.08 | 1.0 | 5 |

EXAMPLES 27 to 30 and COMPARATIVE EXAMPLES 20 to 26

The emulsions having various compositions as shown in Table 11 (as the fungicide, the same fungicide as used in Examples 23 to 26 was employed) were applied to the foliage of Chinese cabbages having a leaf age of 3.5 (11 days after seeding) in an application rate of 100 liter/10 a. Three days later, the phytotoxicity appeared on the leaf surface was examined and classified into five levels (i.e. index numbers 0 to 5 where 0 indicates that no phytotoxicity appeared, and 5 indicates that the phytotoxicity appeared on the entire leaf surface). The phytotoxicity degree was calculated from the results of the evaluation in accordance with the following formula:

$$\text{Phytotoxicity degree} = \frac{\Sigma(\text{Number of leaves of each level} \times \text{Index number})}{\text{Total number of leaves} \times 5} \times 100\ (\%)$$

The results thereby obtained are shown in Table 11. From the results, it is evident that the phytotoxicity caused by the single use of the machine oil emulsifiable concentration or the phytotoxicity caused by the combined use of the machine oil emulsifiable concentration with the fungicide, can be reduced to some extent by the presence of urea, whereas the effectiveness for the reduction of the phytotoxicity is more distinct in the case where the sucrose fatty acid ester was present, and the effectiveness is further improved by the combined use of the sucrose fatty acid ester with urea.

TABLE 11

| | Composition of emulsions for application | | | | |
|---|---|---|---|---|---|
| | Machine oil emulsifiable concentration (%, v/v) | Bactericide (%, w/v) | SE-3 (%, w/v) | Urea (%, w/v) | Phytotoxicity rate (%) |
| Comparative Example 20 | 1.0 | — | — | — | 2.3 |
| Comparative Example 21 | — | — | 0.2 | — | 0.0 |
| Example 27 | 1.0 | — | 0.2 | — | 0.0 |
| Comparative Example 22 | 1.0 | — | — | 1.0 | 1.7 |
| Example 28 | 1.0 | — | 0.2 | 1.0 | 0.0 |
| Comparative Example 23 | — | 1.0 | — | — | 0.0 |
| Comparative Example 24 | 1.0 | 1.0 | — | — | 67 |
| Example 29 | 1.0 | 1.0 | 0.2 | — | 49 |
| Comparative Example 25 | 1.0 | 1.0 | — | 1.0 | 62 |
| Example 30 | 1.0 | 1.0 | 0.2 | 1.0 | 40 |
| Comparative Example 26 | No treatment | | | | 0.0 |

EXAMPLES 31 to 33 and COMPARATIVE EXAMPLES 27 and 28

The effectiveness for the reduction of the phytotoxicity to Satsuma mandarine orange trees of 16 years old was tested with respect to short interval application of the sucrose fatty acid ester and the machine oil emulsifiable concentration.

The solutions for the first application as shown in Table 12 were prepared by using SE-3, urea and a fungicide (the same fungicide as used in Examples 23 to 26) For each test, one branch of the orange tree was used. The five solusions for the first application were applied to the respective five branches. Five days later, the emulsion of the machine oil emulsifiable concentrate was prepared as identified in Table 12 and applied to each branch as the second application. On the 8th day after the second application, the rate of formation of oil specks on the leaf surface was examined. The rate of formation of oil specks is presented in Table 12 as the phytotoxicity rate.

From the results, shown in Table 12, it is evident that when the sucrose fatty acid ester is applied prior to the application of the machine oil, the effectiveness for the reduciton of the phytotoxicity is obtainable, when urea and the sucrose fatty acid ester are used in combination, this effectiveness is further increased. Further, it has been found that the sucrose fatty acid ester is effective to suppress the phytotoxicity rate which was increased by the short interval application of the fungicide and the machine oil emulsifiable concentration.

TABLE 12

|  | First application | | | Second application Machine oil emulsifiable concentration (%, v/v) | Phytotoxicity rate (%) |
| --- | --- | --- | --- | --- | --- |
|  | SE-3 (%, w/v) | Urea (%, w/v) | Bactericide (%, w/v) | | |
| Comparative Example 27 | — | — | — | 0.7 | 97 |
| Example 31 | 0.08 | — | — | 0.7 | 67 |
| Example 32 | 0.08 | 0.4 | — | 0.7 | 63 |
| Comparative Example 28 | — | — | 0.2 | 0.7 | 100 |
| Example 33 | 0.08 | — | 0.2 | 0.7 | 87 |

EXAMPLES 34 and 35 and COMPARATIVE EXAMPLES 29 to 36

The machine oil emulsifiable concentration and various surfactants as identified in Table 13 were diluted with water to bring their concentrations to those identified in Table 13, and they were dissolved to obtain emulsions for application. For each test, two stamps of cucumber of about 6–7 leaf stage were used. On the 7th day after the application of the emulsions, the degree of the phytotoxicity appeared on the leaves and the photosynthesis rate were examined. The degree of the phytotoxicity was evaluated in accordance with the evaluation standards of Table 14 with respect to the 4th to 8th leaves, i.e. a total of 8 leaves. The photosynthesis rate was measured in the same manner as in Examples 12 to 14 by using a closed micro chamber in stead of the phytotoron with respect to the 4th leaf of one of the two stamps of each test.

The results are shown in Table 13. From the results, it is evident that the sucrose fatty acid ester is superior to other surfactants in the effectiveness for the reduction of the phytotoxicity, and such effectiveness is particularly remarkable with respect to the photosynthesis rate.

TABLE 13

| | Agricultural chemicals | | Photosynthesis rate (mg $CO_2$ $dm^{-2}$ $hr^{-1}$) |
| --- | --- | --- | --- |
|  | Machine oil emulsifiable concentration (%, v/v) | Surfactant (%, v/v) | Degree of phytotoxicity |  |
| Comparative Example 29 | — | — | — | 22.6 |
| Comparative Example 30 | 1 | — | ++ | 16.0 |
| Example 34 | 1 | SE-3 (0.1) | + | 21.4 |
| Example 35 | 1 | SE-3 (0.01) | ++ | 19.4 |
| Comparative Example 31 | 1 | Polyoxyethylene sorbitane monooleate (0.1) | +++ | 16.8 |

TABLE 13-continued

| | Agricultural chemicals | | Photosynthesis rate (mg $CO_2$ $dm^{-2}$ $hr^{-1}$) |
| --- | --- | --- | --- |
|  | Machine oil emulsifiable concentration (%, v/v) | Surfactant (%, v/v) | Degree of phytotoxicity |  |
| Comparative Example 32 | 1 | Polyoxyethylene sorbitane monooleate (0.01) | +++ | 17.9 |
| Comparative Example 33 | 1 | Polyethylene glycol monostearate (0.1) | + | 17.6 |
| Comparative Example 34 | 1 | Polyethylene glycol monostearate (0.01) | +++ | 15.0 |
| Comparative Example 35 | 1 | Polyoxyethylene oleyl ether (0.1) | +++ | 17.3 |
| Comparative Example 36 | 1 | Polyoxyethylene oleyl ether (0.01) | +++ | 14.5 |

TABLE 14

| Degree of phytotoxicity | Evaluation standard |
| --- | --- |
| +++ | Oil specks and color change-substantial |
| ++ | Oil specks and color change-distinctly observed |
| + | Oil specks-slightly observed |

EXAMPLES 36 to 40 and COMPARATIVE EXAMPLE 37

The acaricidal effects of the compositions comprising the machine oil emulsifiable concentration and various sucrose fatty acid esters as identified in Table 15 were tested by a leaf disc method in a constant temperature room at 25°C. Water was put in an ice cream cup, and a filter paper with cut lines was placed in the ice cream cup so that the cut line portions were in contact with water. Another filter paper was placed thereon, and two leaf discs prepared by cutting a Satsuma mandarine orange leaf to form a disc having a diameter of 12 mm, were placed in each cup. On each disc, about 10 acarines were placed. Next day, after confirming the number of acarines settled on the discs, the emulsions containing 0.028% (w/v) of various sucrose fatty acid esters as identified in Table 15 and 0.35% (v/v) of the machine oil emulsifiable concentrate, were applied to the respective cups at a application rate of 50 mg/cm². Next day, the number of dead acarines on each leaf and the number of escaped acarines were counted, and the acaricidal rate was calculated in accordance with the following formula:

$$\text{Acaricidal rate} = \frac{\text{Number of dead acarines}}{\text{Number of settled acarines} - \text{Number of escaped acarines}} \times 100$$

The results thereby obtained are shown in Table 15. From the results, it is evident that all of the compositions of the present invention have remarkable acaricidal effects, although the acaricidal rates vary depending upon the type of the sucrose fatty acid ester used.

TABLE 15

| | Cane sugar esters | Acaricidal rates (%) |
|---|---|---|
| Example 36 | SE-1 | 86.5 |
| Example 37 | SE-2 | 94.6 |
| Example 38 | SE-3 | 94.0 |
| Example 39 | SE-5 | 53.4 |
| Example 40 | SE-6 | 97.6 |
| Comparative Example 37 | — | 46.7 |

We claim:

1. An emulsifiable insecticidal and acaricidal concentrate, which comprises:
   100 parts by weight of an agricultural machine oil and from 0.1 to 50 parts by weight of a sucrose fatty acid ester.

2. The composition according to claim 1, which contains from 0.5 to 20 parts by weight of the sucrose fatty acid ester per 100 parts by weight of the agricultural machine oil.

3. The compostion according to claim 1, which comprises 100 parts by weight of the agricultural machine oil, from 0.1 to 50 parts by weight of the sucrose fatty acid ester and from 1 to 300 parts by weight of urea.

4. The composition according to claim 3, which contains from 5 to 100 parts by weight of urea per 100 parts by weight of the agricultural machine oil.

5. The composition according to claim 1, wherein the sucrose fatty acid ester has a HLB of from 9 to 17.

6. The composition according to claim 5, wherein the fatty acid moiety of the sucrose fatty acid ester has from 14 to 18 carbon atoms, and the monoester content in the ester is from 40 to 80%.

7. An emulsifiable insecticidal and acaricidal concentrate, which comprises: 100 parts by weight of an agricultural machine oil, from 0.1 to 50 parts by weight of a sucrose fatty acid ester and from 1 to 300 parts by weight of urea.

* * * * *